(12) United States Patent
Deaton et al.

(10) Patent No.: US 6,870,054 B1
(45) Date of Patent: Mar. 22, 2005

(54) SYNTHESIS FOR ORGANOMETALLIC CYCLOMETALLATED TRANSITION METAL COMPLEXES

(75) Inventors: Joseph C. Deaton, Rochester, NY (US); Richard L. Parton, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/729,263

(22) Filed: Dec. 5, 2003

(51) Int. Cl.[7] .................. C07F 15/00; B32B 9/00
(52) U.S. Cl. .................. 546/10; 549/3; 556/40; 556/41; 556/136; 257/40; 428/690
(58) Field of Search .................. 257/40; 428/690; 546/10; 549/3; 556/3, 40, 41, 136

(56) References Cited

U.S. PATENT DOCUMENTS 6,670,645 B2 * 12/2003 Grushin et al. .............. 257/98
2002/0190250 A1   12/2002 Grushin et al. .............. 257/40
2003/0068526 A1    4/2003 Kamatani et al. ........... 428/690
2003/0096138 A1 *  5/2003 Lecloux et al. ............. 428/690

FOREIGN PATENT DOCUMENTS

WO      WO 02/060910       8/2002

OTHER PUBLICATIONS

Constable et al., Inorganica Chemica Acta, vol. 235, No. 1–2, pp. 165–171 (1995).*

* cited by examiner

*Primary Examiner*—Porfirio Nazario-Gonzalez
(74) *Attorney, Agent, or Firm*—Arthur E. Kluegel

(57) ABSTRACT

Disclosed is a process for forming an organometallic cyclometallated iridium compound comprising reacting an iridium halide complex with a silver salt and excess organic cyclometallating ligand in a diol solvent. The process provides better yields and control of desired isomers.

41 Claims, No Drawings

SYNTHESIS FOR ORGANOMETALLIC CYCLOMETALLATED TRANSITION METAL COMPLEXES

FIELD OF THE INVENTION

This invention relates to the field of organic synthesis and to a process for forming organometallic cyclometallated complexes of Ir(III) comprising the step of reacting a halide-containing complex of the metal with a silver salt and a heterocyclic organic ligand compound capable of forming an organometallic cyclometallated complex and in a solvent comprising an organic diol.

BACKGROUND OF THE INVENTION

Organometallic cyclometallated complexes of transition metals (e.g. rhodium, iridium, platinum) have become useful materials because of their photophysical and photochemical properties. One especially important application of these compounds are as phosphorescent dopants in Organic Light-Emitting Diodes because of their strong emission from triplet excited states (M. A. Baldo, et al, *Appl. Phys. Letters,* 75, 4 (1999)). An important class of phosphorescent organometallic cyclometallated complexes contain ligands that are at least bidentate wherein one coordination site of the ligand to the metal is through an N atom that is doubly bonded to C or another N atom, usually as part of a heterocyclic ring, and wherein another coordination site of the ligand to the metal is through a C atom. As used herein, the term "organometallic cyclometallated complex" means that at least one of the coordination sites forming the cyclic unit binding the metal atom by at least one ligand must be a metal-carbon bond. The metal-carbon bond is formed in place of a hydrogen-carbon bond of the free ligand before it is complexed. The carbon atom forming the metal carbon bond is usually also doubly bonded to another carbon as in, for example, a phenyl ring or a thienyl ring or furanyl ring. Further the carbon atom forming the metal-carbon bond also is preferably positioned so as to form a five or six-membered metallacycle including the coordinated N atom of the ligand. Some examples of iridium(III) organometallic cyclometallated complexes are shown below.

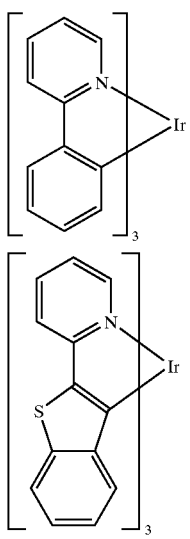

Further, there are two isomers, facial and meridional (fac and mer), possible for such complexes having three identical but unsymmetrical bidentate ligands as illustrated below. The facial isomers are typically more desirable in OLED applications for having higher quantum yields.

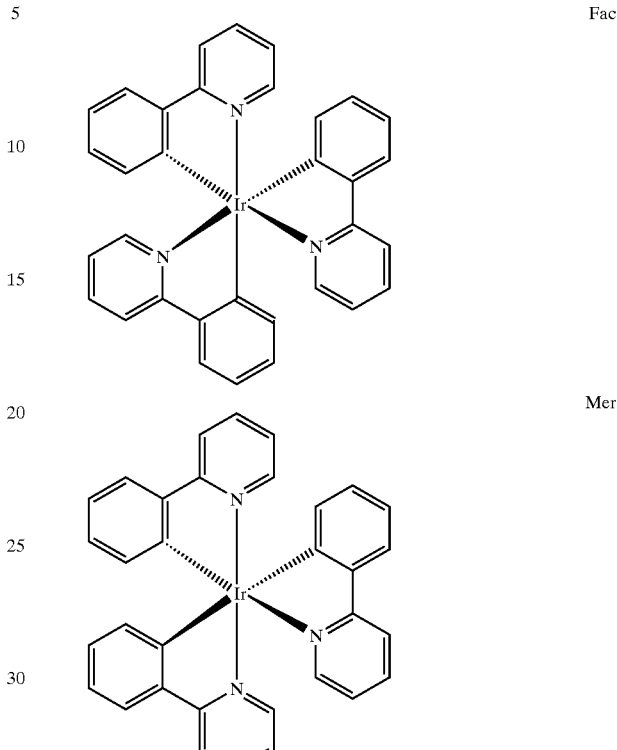

It is also possible that the organometallic cyclometallating ligands are not all the same. Further, the organometallic cyclometallated complex must have at least one cyclometallating ligand forming a metal-carbon bond, but may have additional types of ligands not forming metal-carbon bonds. A common type of the latter would be complexes of the form $L_2MX$ as described in WO 02/15645 A1. Here L is a cyclometallating ligand forming metal-carbon and metal-nitrogen bonds, while X is another monoanionic bidentate ligand that does not form metal carbon bonds, such as acetylacetonate.

The usefulness and importance of organometallic cyclometallated complexes of second- and third-row transition metals have necessitated synthetic methods for preparing them more efficiently. Chassot et al., *Inorg. Chem.,* 1984, 23,4249–4253, have used lithiated ligands with platinum compounds that include leaving groups to form cyclometallated complexes of the ligands with platinum. Jolliet et al., *Inorg. Chem.,* 1996, 35, 4883–4888, also used lithiated ligands to form cyclometallated complexes of the ligands with platinum or palladium, and Lamansky and Thompson, in International Patent Application WO 00/57676, used the same procedure for cyclometallated platinum complexes. These procedures suffer from low yields, as well as the relative instability of and difficulty in handling lithiated organic materials.

Organometallic cyclometallated complexes may also be formed from direct reaction of the cyclometallating ligand, wherein the carbon-hydrogen is activated and replaced by the carbon-metal bond. For example, fac-tris(2-phenylpyridinato-N,$C^{2'}$)iridium(III), or Ir(ppy)$_3$, was made by reaction of 2-phenylpyridine and tris(acetylacetonate)

iridium (Ir(acac)₃) in glycerol solvent by K. Dedian et al, *Inorg. Chem.*, 30, 1685 (1991). Sto(e)ssel et al (WO 02/060910 A1) further optimized and improved this reaction, but still using the expensive Ir(acac)₃ starting material. By reacting less expensive halide complexes of Ir(III) such as iridium(III) chloride hydrate with 2-phenylpyridine in a solvent comprising a 3:1 mixture of 2-ethoxy-ethanol and water, Nonoyama obtained dimeric organometallic cyclometallated complexes such as tertakis (2-phenyl -pyridinato-N,C²'-) (di-μ-chloro)di-iridium(III). (Note: Ir(ppy)₃ was later extracted as a side product in 10% yield from this reaction mixture, K. A. King, et al, *J. Am. Chem. Soc.*, 107, 1431 (1985).) This particular solvent and the related 2-methoxy-ethanol are not desirable for practical use due to adverse health effects. M. G. Colombo, et al *Inorg Chem.*, 33, 545 (1994), further reacted the above-cited di-iridium complex with a silver salt in neat 2-phenylpyridine to obtain Ir(ppy)₃ in 75% yield. Grushin et al US 2002/0190250 A1 used this process to make additional tris-cyclometalated complexes of Ir(III) having fluorine-substitutions on phenylpyridine and phenylquinoline cyclometallating ligands. But this process requires a large excess of a ligand since it is employed as the solvent, thereby either consuming valuable material or necessitating a process to recover excess ligand.

Lamasky et al., *Inorg. Chem.*, 2001, 40, 1704–1711, demonstrated yet another process for making tris-cyclometallated Iridium complexes. First, a mixed ligand complex bis(7,8-benzoquinolinato-N,C³') iridium(III) (acetylacetonate) was made from tetrakis(7,8-benzoquinolinato-N,C³') di-μ-chloro)di-iridium(III). Then the bis(7,8-benzoquinolinato-N,C³') iridium(III) (acetylacetonate) was reacted with additional 7,8-benzoquinoline in refluxing glycerol to produce a mixture of isomers of the tris-cyclometallated complex, tris(7,8-benzoquinolinato-N,C³')iridium(III). Kamatani et al, US 2003/0068526 A1, have also employed this reaction type for additional cyclometallated iridium complexes. But this process often yields less-desireable meridional isomers or mixtures of the facial and meridonal isomers of the tris-cyclometallated complexes. Tamayo et al., *J. Am. Chem. Soc.*, 125, 7377–7387 (2003), have shown that reaction of dimeric organometallic cyclometallated complexes such as tetrakis(2-phenyl-pyridinato-N,C²'-) (di-μ-chloro)di-iridium (III) with sodium carbonate and additional cyclometallating ligand in glycerol can lead to formation of meridional isomers in many cases, while further reaction at higher temperatures results in formation of mostly facial isomer. However, this procedure is inconvenient for facial isomers as it necessitates finding exact conditions for the reaction of each ligand.

Despite the large number of investigations into the synthetic methodology for cyclometallated complexes, there remains a need for methods that provide better yields and control of desired isomers.

SUMMARY OF THE INVENTION

The invention provides a process for forming an organometallic cyclometallated iridium compound comprising reacting an iridium halide complex with a silver salt and excess organic cyclometallating ligand in a diol solvent.

The process provides better yields and control of desired isomers.

DETAILED DESCRIPTION OF THE INVENTION

The invention is summarized above. The process reacts an iridium halide complex with the neutral, uncomplexed form of the cyclometallating ligand to form a diiridium cyclometallated complex containing bridging halides and having formula (1):

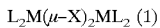

L₂M(μ-X)₂ML₂ (1)

wherein L is a bidentate cyclometallating ligand and (μ-X) represents a bridging halide, and then further reacting this intermediate diiridium complex with additional ligand and a silver salt in a solvent comprising a diol. Both steps of the process may optionally be carried out sequentially in the same reaction vessel without first isolating the diiridium intermediate complex. The option of performing both steps in the same reaction vessel provides convenience and simplification, as long as enough silver salt is added to consume all the halide from the starting material. Alternatively, the diiridium cyclometallated complex formed in the first step comprising the reaction of the cyclometallating ligand with the iridium halide complex may be isolated first, before further reacting in a second step with a soluble silver salt in a solvent comprising a diol. In this embodiment, the formation of the diiridium cyclometallated complex may be carried out according to the procedure of M. Nonoyama, *Bull. Chem. Soc. Jpn.*, 47,767 (1974) in which a solvent such as 2-methoxy-ethanol or 2-ethoxy-ethanol in a 3:1 mixture with water is employed. However, there are significant health hazards with the solvents 2-methoxy-ethanol and 2-ethoxy-ethanol, and therefore it is preferable to use the solvents of this invention for the formation of the diiridium cyclometallated complex as well. Further, it will be appreciated that in the embodiement wherein a diiridium cyclometallatewd complex is isolated first, and subsequently reacted with additional cyclometallating ligand and a silver salt in a diol solvent, that the additional cyclometallating ligand may be the same or different from the one already complexed in the starting diiridium cyclometallated complex.

Yet another object of this invention is to provide a process for forming an organometallic cyclometallated iridium compound comprising reacting a complex of the type L₂IrX with excess organic cyclometallating ligand L' and in a diol solvent, wherein L is a cyclometallating ligand forming metal-carbon and metal-nitrogen bonds, while X is a monoanionic bidentate ligand that does not form metal carbon bonds, and L' is an organic cyclometallating ligand that may be the same or different from L. The complexes of the type L2IrX may be formed as described in WO 02/15645 A1.

The halide complexes of IR(III) useful in the invention may be any halide complex or salt thereof, such as for example, iridium(III) chloride hydrate, iridium(III) bromide hydrate, tripotassium hexachloroiridate(III) or tripotassium hexachloroiridate(III). Halide complexes of Ir(IV) may also be used in the invention since these can be readily reduced in the reaction mixture. Examples include dipotassium hexchloroiridate(IV) and dipotassium hexabromoiridate (IV).

The solvents useful in this invention comprise diols. These solvents provide a suitable medium for the organometallic cyclometallation reactions, but are less viscous than for example, glycerol, and therefore it is easier to perform such operations as transfer and filtering. The diol solvents of the present invention also avoid health hazards associated with the 2-methoxy- or 2-ethoxy-ethanol solvents that are frequently used for the cyclometallation reactions. Solvents useful in the invention also provide high product yields and high isomeric purity. The reaction mixtures may be conveniently heated to the reflux temperature of the solvent, or may be held in a constant temperature bath. The preferred temperature range for the reactions is 140 to 220° C. Examples of solvents useful in the invention include, but are not limited to the following:

Ethylene glycol
1,2-propanediol
1,3-propanediol
1,3-butanediol
catechol

Silver salts useful in the invention include soluble salts with an anion such as tetrafluoroborate, trifluoroacetate, or trifluoromethanesulfonate. It is also possible to use other metal ion salts in the process of the invention if the metal ions form insoluble compounds with halide ions. Examples would be salts of thallium. However, thallium salts are not suitable for manufacturing processes due to the toxic effects of thallium. The reaction vessel may be initially charged with all of the silver salt needed for the reaction, or the silver salt may be added slowly as a solution in additional reaction solvent during the course of the reaction to avoid high concentrations of silver that may lead to reduction of silver. Furthermore, in one embodiment of this invention where the two reaction steps are conducted sequentially in the same reaction vessel, without isolating the intermediate diiridium complex, the silver salt may all be added in the initial set-up of the reaction vessel, or may be added to the reaction vessel after the first reaction step to form the intermediate diiridium cyclometallated complex is completed.

It is preferable to carry out the process of the invention under an atmosphere of inert gas from which oxygen is excluded to avoid the risk of undesired decomposition reactions with oxygen. The inert gases commonly used for such purposes are nitrogen or argon, but may also be other inert gases such as helium. One simple way to establish the inert atmosphere is to purge the inert gas through the reaction vessels and solvents before starting the reaction. On a small scale, it is also convenient to use a freeze-thaw degas technique in which the initial reaction vessel charged with the starting materials and solvent is frozen while the air is removed by vacuum, followed by introduction of the inert gas atmosphere.

Embodiments of the invention can provide more convenient methods employing less expensive starting materials and solvents that are applicable to a wide range of cyclometallating ligands.

The invention and its advantages can be better appreciated by the following examples.

EXAMPLE 1

Preparation of fac-tris(2-phenylpyridinato-N,$C^{2'}$) iridium(III)

$K_3IrBr_6$ (7.75 g, 9.82 mmol) was placed in a 200 mL flask with 75 mL 2-ethoxyethanol, 25 mL water, and 2-phenylpyridine (4.2 mL). The mixture was freeze-thaw degassed, and then refluxed for 4 hrs under nitrogen atmosphere during which time a yellow-orange precipitate appeared. After cooling, the precipitate was filtered, washed with 1 N HBr(aq), then water, and dried. Yellow tetrakis(2-phenylpyridine-N,$C^{2'}$)($\mu$-dibromo)diiridium(III) (5.018 g) was collected (88% yield based on iridium). This intermediate material was used without further purification in the subsequent step.

Tetrakis(2-phenylpyridine-N,$C^{2'}$)($\mu$-dibromo)diiridium (III) (0.960 g) and silver trifluoroacetate (0.54 g) were placed in a 100 mL flask. 1,2-Propanediol (35 mL) and 2-phenylpyridine (0.75 mL) were added and the mixture was freeze-thaw degassed and then refluxed under nitrogen for 5 hours. After cooling, the mixture was poured in air into 150 mL 1 molar HBr(aq). The yellow precipitate was filtered, washed with water, and dried. The crude product was sublimed to give yellow-orange powder and crystals (0.982 g) for a 91% yield based on iridium. Analysis by HPLC and combined LC/MS techniques showed the product was fac-tris(2-phenylpyridinato-N,$C^{2'}$)iridium(III) containing only a trace of the meridional isomer.

EXAMPLE 2–7

Additional Preparations of fac-tris(2-phenylpyridinato-N,$C^{2'}$) iridium(III)

Examples 2 thru 7 were carried out in a similar manner to Example 1 except the solvent was changed as listed in Table 1. An additional difference for Examples 3 and 5 was that iridium(III) chloride hydrate was used as the starting material, and hence the intermediate formed in an analogous manner was tetrakis(2-phenylpyridine-N,$C^2$)($\mu$-dichloro) diiridium(III). The results shown in Table 1 show that the process with solvents of the invention provide higher yield and better isomeric purity than comparison examples using other solvents, including those commonly found in the prior art of cyclometallation reactions. Example 2 compared to Example 3 further shows that while iridium chloride complexes may be used in the invention as starting materials, better yields may be obtained with the bromide complexes as starting materials.

TABLE 1

| Example | Example Type | Halide | Solvent | Yield (%) | Mer Isomer (%) |
|---------|--------------|--------|---------|-----------|----------------|
| 1 | Invention | Br | 1,2-Propanediol | 91 | Trace |
| 2 | Invention | Br | 1,3-Butanediol | 89 | 0.5 |
| 3 | Invention | Cl | 1,3-Butanediol | 78 | N.A. |
| 4 | Invention | Br | Ethyleneglycol | 91 | 1.4 |
| 5 | Comparison | Cl | 2-Ethoxyethanol | 56 | 0.8 |
| 6 | Comparison | Br | Glycerol | 75 | 14 |
| 7 | Comparison | Br | 1-Octanol | 66 | Trace |

EXAMPLE 8

Additional Preparation of fac-tris(2-phenylpyridinato-N,$C^{2'}$) iridium(III)

This example was also carried out in a similar fashion to example 1, except the solvent was 1,3-propanediol. The yellow precipitate collected was dissolved in dichloromethane and filtered to remove insoluble silver and/or silver salts, and then precipitated by evaporating the solvent. The yield was 92% of tris(2-phenylpyridinato-N,$C^{2'}$)iridium (III), of which the majority was the facial isomer and only 1.2% was identified as the meridional isomer.

EXAMPLE 9

Synthesis of fac-tris(2-phenylpyridinato-N,$C^{2'}$) iridium(III) In One Vessel.

This example was performed in the same manner as example 4 except that both steps in the reaction sequence were carried out sequentially in the same reaction vessel without isolating the intermediate compound and using the 1,3-butanediol solvent from the beginning.

2-Phenylpyridine (1 mL, 1.09 g, 7.0 mmol) and $IrCl_3 \cdot 3H_2O$ (350 mg, 1.0 mmol) were combined with 8 mL of 1,3-butanediol in a 50 mL flask equipped with a magnetic stirrer, condenser and $N_2$ inlet. The mixture was heated in an oil bath at 170–175° C. for 2 hrs with magnetic stirring. A yellow solid formed almost immediately. Silver trifluoroacetate (880 mg, 4.0 mmol) was dissolved in ~2 mL of 1,3-butanediol and this material was added to the hot reaction mixture using a disposable pipette. A reaction appeared to take place immediately, the yellow solid appeared to dissolve and a new yellow solid appeared to form. The mixture was heated at 170–175° C. for an additional 3.5 hr. The heat was removed and after cooling a yellow solid was collected by filtration, washed with ethanol, and dried (1.07 g). This material was sublimed in a tube furnace with nitrogen entrainment gas (330° C., 0.7 Torr) to afford 510 mg of product fac-tris(2-phenylpyridinato-N,$C^2$)iridium (III) (78% yield). NMR matched the published spectrum.

EXAMPLE 10

Preparation of fac-tris-(2-(2'-benzothienyl) pyridinato)Ir(III)

2-(2'-Benzothienyl)pyridine was synthesized according to literature procedures (K. E. Chippendale, B. Iddon, and H. Suschitzky, Journal of the Chemical Society [Section D]: Chemical Communications (1971), 4, 203–4).

$K_3IrBr_6$ (5.05 g, 6.40 mmol Ir) and 2.5 equiv 2-(2'-benzothienyl)pyridine (3.42 g) were placed in a 200 mL r.b. flask with 45 mL of 2-ethoxy-ethanol and 15 mL water. The mixture was freeze-thaw degassed and then refluxed under a nitrogen atmosphere for 6 h. After cooling, a red-orange solid was collected by filtration, washed with 1N HBr(aq) and water, then dried to give 4.23 g of the crude product tetrakis(2-(2'-benzothienyl)pyridinato-N,$C^3$)($\mu$dibromo) diiridium(III) (95% yield). This material was used without further purification.

A portion of the tetrakis(2-(2'-benzothienyl)pyridinato-N, $C^3$)di-$\mu$1-bromo-diiridium (III) complex thus prepared (1.20 g) and 2-(2'-benzothienyl)pyridine (0.914 g), and silver trifluoroacetate (0.459 g) were placed under a nitrogen atmosphere in a 2-neck r.b. flask equipped with a reflux condenser and a rubber septum. 1,3 Butanediol (30 mL) was freeze-thaw degassed in a separate flask and transferred via cannula to the reaction flask. The mixture was refluxed under a nitrogen atmosphere for 5 h. After cooling, an orange-red solid was collected by filtration in air, washed with 1 N HBr(aq) and water, and dried (1.65 g). This crude material was triturated with diethyl ether and methanol to remove free ligand, affording 1.435 g after drying. This material was dissolved into 30–40 mL $CH_2Cl_2$ giving a dark red-orange solution with some gray insolubles. The solution was gravity filtered through a short column of silica gel in methylene chloride. The resulting solution was concentrated until a red-orange solid began to precipitate. Then the rest of the product was driven out of solution by layering heptane and refrigerating. The precipitate was collected by filtration and dried, 0.990 g, 70% yield. The mass spectrum showed parent ion peaks of 822 and 824 amu, corresponding to the two Ir isotopes and confirming the formula tris-(2-(2'-benzothienyl)pyridinato)Ir(III). Part of this material was sublimed at 295–305° C. in a tube furnace with nitrogen entrainment gas to yield red-orange crystals. Analysis by HPLC demonstrated that the sublimation had not caused the material to isomerise. Single crystal x-ray structure determination confirmed that the product was the fac isomer.

EXAMPLE 11

Preparation of mer-tris-(2-(2'-benzothienyl) pyridinato)Ir(III)

Tetrakis(2-(2'-benzothienyl)pyridinato-N,$C^3$)di-$\mu$-bromo-diiridium(III) (1.64 g,) prepared as in Example 10 was placed in a 100 mL r.b. flask with $Na_2CO_3$ (1.25 g). 30 mL 2-ethoxyethanol was added, then 2,4-pentanedione (0.48 g). The mixture was freeze-thaw degassed, then refluxed under $N_2$ 18 hrs. A dull orange solid was filtered from the dark brown solution, washed with water, and then dried (0.686 g). Analytical data was consistent with the product as bis(2-(2'-benzothienyl)pyridinato-N,$C^3$)(acetylacetonato)iridium(III) This material was used without purification for the next reaction.

Bis(2-(2'-benzothienyl)pyridinato-N,$C^3$) (acetylacetonato)Iridium(III) (0.68 g; 0.954 mmole Ir) as prepared above was placed in a 50 mL r.b. flask with 2-(2'-benzothienyl)pyridine (0.504 g) and about 20 mL 1,3-butanediol. The mixture was freeze-thaw degassed, then refluxed under $N_2$ 24 hrs. After cooling, a dull red-orange solid was filtered, washed, and dried (0.499 g). The mass spectrum showed parent ion s of 822 amu, confirming the formula tris-(2-(2'-benzothienyl)pyridinato)Ir(III). HPLC showed a peak that gave a broad emission at 595 nm but that had a different retention time from that of fac-tris-(2-(2'-benzothienyl)pyridinato)Ir(III) prepared in Example 10. The difference in retention time of the two materials was confirmed by mixing solutions together and observing the two separate peaks in the HPLC and thereby also indicating that the present crude material consisted of the meridional isomer of tris-(2-(2'-benzothienyl)pyridinato)Ir(III). The crude product was washed with diethyl ether. Then the product was then dissolved in $CH_2Cl_2$ (50 mL) and passed thru a short column of silica gel (15 g) in the same solvent. The red-orange solution was concentrated and then precipitated by addition of hexanes. An orange powder was collected and dried (280 mg). A portion of this product was sublimed in a tube furnace with $N_2$ entrainment gas at 288–295° C. Red-orange crystals were recovered. A single-crystal x-ray diffraction study confirmed the structure of mer -tris-(2-(2'-benzothienyl)pyridinato)Ir(III), while HPLC analysis showed that the crystals obtained by sublimation were the same substance as the orange powder before sublimation.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

What is claimed is:

1. A process for forming an organometallic cyclometallated iridium compound comprising reacting an iridium halide complex with a silver salt and excess organic cyclometallating ligand in a diol solvent.

2. The process of claim 1 wherein the diol solvent has a boiling point in the range of 140–220° C.

3. The process of claim 1 wherein the diol solvent has 2 to 6 carbon atoms.

4. The process of claim 1 wherein the diol is an aromatic diol.

5. The process of claim 4 where the aromatic diol is catechol.

6. The process of claim 1 where the diol solvent is selected from the group consisting of 1,2-propanediol, 1,3-propanediol, and 1,3-butanediol.

7. The process of claim 1 where the diol solvent is ethylene glycol.

8. The process of claim 1 where the silver salt is selected from silver tetrafluoroborate, silver trifluoroacetate, or silver trifluoromethanesulfonate.

9. The process of claim 1 where the iridium halide complex is selected from tripotassium hexachloroididate (III) or tripotassium hexabromoiridate(III).

10. The process of claim 1 where the iridium halide complex is selected from iridium(III) chloride hydrate or iridium(III) bromide hydrate.

11. The process of claim 1 where the iridium halide complex is selected from dipotassium hexachloroididate(IV) or dipotassium hexabromoiridate(IV).

12. A process for forming an organometallic cyclometallated iridium compound comprising reacting a dimeric iridium complex containing bridging halides with a silver salt and an organic cyclometallating ligand and in a diol solvent, wherein the dimeric iridium complex is of Formula (1):

L$_2$Ir(u–X)$_2$IrL$_2$ (1)

wherein:

L is a bidentate cyclometallating ligand; and

X is a halide.

13. The process of claim 12 wherein the diol solvent has a boiling point in the range of 140–220° C.

14. The process of claim 12 wherein the diol solvent has 2 to 6 carbon atoms.

15. The process of claim 12 wherein the diol is an aromatic diol.

16. The process of claim 15 where the aromatic diol is catechol.

17. The process of claim 12 where the diol solvent is selected from the group consisting of 1,2-propanediol, 1,3-propanediol, and 1,3-butanediol.

18. The process of claim 12 where the diol solvent is ethylene glycol.

19. The process of claim 12 where the silver salt is selected from silver tetrafluoroborate, silver trifluoroacetate, or silver trifluoromethanesulfonate.

20. A process for forming a dimeric iridium complex containing bridging halides of comprising reacting an iridium halide complex with an organic cyclometallating ligand in a diol solvent, wherein the dimeric iridium complex containing bridging halides is represented by Formula (1):

L$_2$Ir(u–X)$_2$IrL$_2$ (1)

wherein:

L is a bidentate cyclometallating ligand; and

X is a halide.

21. The process of claim 20 wherein the diol solvent has a boiling point in the range of 140–220° C.

22. The process of claim 20 wherein the diol solvent has 2 to 6 carbon atoms.

23. The process of claim 20 wherein the diol is an aromatic diol.

24. The process of claim 23 where the aromatic diol is catechol.

25. The process of claim 20 where the diol solvent is selected from the group consisting of 1,2-propanediol, 1,3-propanediol, and 1,3-butanediol.

26. The process of claim 20 where the diol solvent is ethylene glycol.

27. The process of claim 20 where the iridium halide complex is selected from tripotassium hexachloroididate (III) or tripotassium hexabromoiridate(III).

28. The process of claim 20 where the iridium halide complex is selected from iridium(III) chloride hydrate or iridium(III) bromide hydrate.

29. The process of claim 20 where the iridium halide complex is selected from dipotassium hexachloroididate(IV) or dipotassium hexabromoiridate(IV).

30. The process of claim 12, wherein the halide is bromide.

31. The process of claim 20, wherein the halide is bromide.

32. The process of claim 1, wherein the iridium halide complex is reacted with excess organic cyclometallating ligand in a diol solvent and then a silver salt is combined with the reaction mixture.

33. A process for forming an organometallic cyclometallated iridium compound comprising reacting a complex of the type L$_2$IrX with excess organic cyclometallating ligand and in a diol solvent, wherein L is a cyclometallating ligand forming metal-carbon and metal-nitrogen bonds, while X is a monoanionic bidentate ligand that does not form metal carbon bonds.

34. The process as in claim 33 wherein X is acetylacetonate.

35. The process of claim 33 wherein the diol solvent has a boiling point in the range of 140–220° C.

36. The process of claim 33 wherein the diol solvent has 2 to 6 carbon atoms.

37. The process of claim 33 wherein the diol is an aromatic diol.

38. The process of claim 37 wherein the aromatic diol is catechol.

39. The process of claim 33 wherein the diol solvent is selected from of 1,2-propanediol, 1,3-propanediol, and 1,3-butanediol.

40. The process of claim 33 wherein the diol solvent is ethylene glycol.

41. The process of claim 1 carrier out as a one-pot reaction.

* * * * *